United States Patent

Nakajima et al.

Patent Number: 4,959,460
Date of Patent: Sep. 25, 1990

[54] 3'-DEAMINO-3'-(2''-SUBSTITUTED-4''-MORPHOLINO)-ANTHRACYCLINE COMPOUNDS

[75] Inventors: Shohachi Nakajima; Nobuyasu Komeshima, both of Maebashi, Japan

[73] Assignee: Kirin Beer Kabushiki Kaisha, Tokyo, Japan

[21] Appl. No.: 400,470

[22] Filed: Aug. 29, 1989

[30] Foreign Application Priority Data

Sep. 2, 1988 [JP] Japan ................................ 63-220203

[51] Int. Cl.⁵ ............................................ C07H 15/24
[52] U.S. Cl. .................................................... 536/6.4
[58] Field of Search ........................... 536/6.4; 514/34

[56] References Cited

U.S. PATENT DOCUMENTS 4,710,564 12/1987 Otake et al. ........................... 536/6.4

Primary Examiner—Ronald W. Griffin
Assistant Examiner—Elli Peselev
Attorney, Agent, or Firm—Ladas & Parry

[57] ABSTRACT

Disclosed is an anthracycline compound of the formula (I):

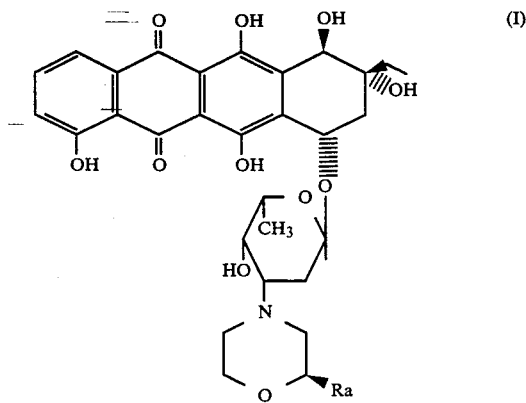

wherein Ra is -R$^1$,

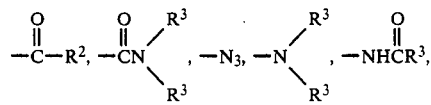

or —OR$^3$, R$^1$ being (1) alkyl, alkenyl, alkynyl, fluoroalkyl, aryl or aralkyl, or (2) alkyl, alkenyl, alkynyl, fluoroalkyl, aryl or aralkyl having carboxyl, azido, amino, hydroxy, alkoxy or a halogen atom; R$^2$ being R$^1$, a hydrogen atom or hydroxy; and R$^3$, which may be the same or different when one substituent has two R$^3$'s, being R$^1$ or a hydrogen atom; or the formula (II):

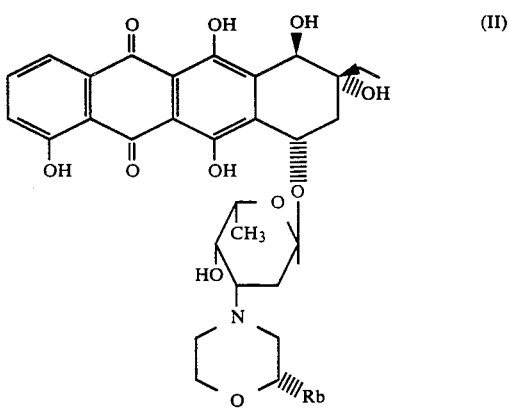

wherein Rb is -R$^1$,

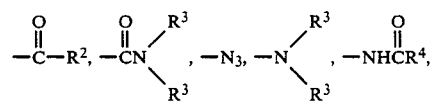

or —OR$^3$, R$^1$, R$^2$ and R$^3$ being as defined above; and R$^4$ being the same as R$^3$ except that methyl is not included; or an acid addition salt thereof.

This compound can be contained as an active ingredient in an antitumor agent, whereby good results are attainable.

6 Claims, No Drawings

3'-DEAMINO-3'-(2"-SUBSTITUTED-4"-MORPHOLINO)-ANTHRACYCLINE COMPOUNDS

BACKGROUND OF THE INVENTION

The present invention relates to a 3'-deamino-3'-(2"-substituted-4"-morpholino) derivative of 13-deoxo-10-hydroxycarminomycin (hereinafter referred to as "R20X2") which is an anthracycline compound having antitumor activity.

Anthracycline compounds heretofore known are, for example, daunomycin (U.S. Pat. No. 3,616,242) and adriamycin (U.S. Pat. No. 3,590,028) obtained from the culture broths of actinomycetes, and these compounds are widely used for clinical purposes as antitumor agents.

Yoshimoto et al. obtained R20X2 which exhibits antitumor activity from the culture broth of Streptomyces sp. D-788 (Japanese Patent Application Laid-Open Pub. No. 33194/1986).

Further, various derivatives of adriamycin, daunomycin and carminomycin were synthesized as morpholino derivatives of anthracycline compounds and have been reported to have antitumor activity (Japanese Patent Application Laid-Open Pub. No. 163393/1982; U.S. Pat. No. 4,301,277; Japanese Patent Application Laid-Open Pub. No. 212484/1984; and Japanese Patent Application Laid-Open Pub. No. 212499/1984).

We also synthesized morpholino derivatives of 13-deoxocarminomycin, 13-deoxo-11-deoxycarminomycin and 13-deoxo-10-hydroxycarminomycin (R20X2) and have reported that these compounds possess remarkable antitumor activity (Japanese Patent Application Laid-Open Pub. Nos. 167696/1986 and 16495/1987 and U.S. Pat. No. 4,710,564).

Anthracycline compounds form a group of useful antitumor agents, so that there has been constant demand for better anthracycline compounds.

SUMMARY OF THE INVENTION

The present invention contributes toward meeting the above-mentioned demand by introducing a substituent on the 2"-position of the morpholino group in the morpholino derivative of R20X2 mentioned above.

More particularly, the anthracycline compound according to the present invention or an acid addition salt thereof is represented by the formula (I) or (II) shown below.

The present invention also relates to uses of the anthracycline compound or an acid addition salt thereof. Thus the antitumor agent according to the present invention comprises as an active ingredient a safe and effective amount of an anthracycline compound of the following formula (I) or (II) or an acid addition salt thereof and a pharmaceutically acceptable carrier.

The present invention further relates to a method of treating tumors in subjects which comprises administering to a subject in need of such treatment a safe and effective amount of an anthracycline compound of the following formula (I) or (II) or an acid addition salt thereof.

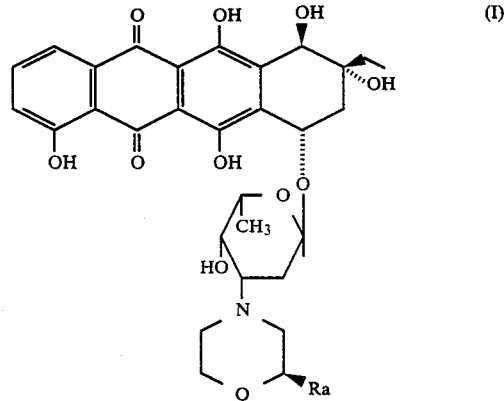

wherein Ra is $-R^1$,

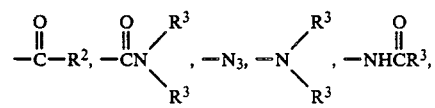

or $-OR^3$, $R^1$ being (1) alkyl, alkenyl, alkynyl, fluoroalkyl, aryl or aralkyl, or (2) alkyl, alkenyl, alkynyl, fluoroalkyl, aryl or aralkyl having carboxyl, azido, amino, hydroxy, alkoxy or a halogen atom; $R^2$ being $R^1$, a hydrogen atom or hydroxy; and $R^3$, which may be the same or different when one substituent has two $R^3$'s, being $R^1$ or a hydrogen atom.

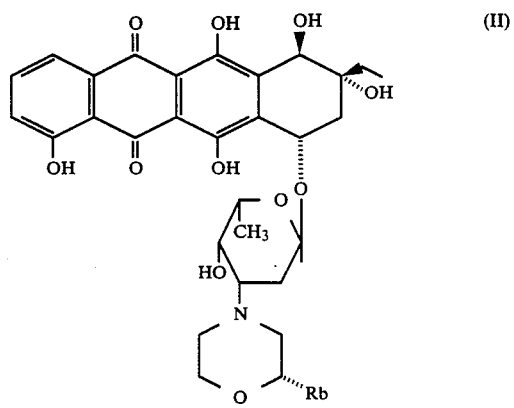

wherein Rb is $-R^1$,

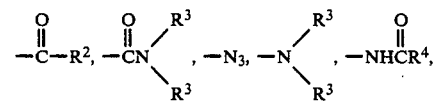

or $-OR^3$, $R^1$, $R^2$ and $R^3$ being as defined above, and $R^4$ being the same as $R^3$ except that methyl is not included.

The anthracycline compound of the present invention has a structure wherein a substituent is introduced on the 2"-position of a morpholino derivative of 13-deoxo-10-hydroxycarminomycin (R20X2) and exhibits even higher antitumor activity against some types of tumors than the base compound, morpholino derivative of R20X2.

DETAILED DESCRIPTION OF THE INVENTION

3'-Deamino-3'-(2"-substituted-4"-morpholino)anthracycline compound

The 3'-deamino-3'-(2"-substituted-4"-morpholino)anthracycline compound according to the present invention is represented by the above shown formula (I) or (II) wherein the substituents are as defined earlier. In the definition of $R^1$, the phrase "(2) . . . having carboxyl, azido, amino, hydroxy, alkoxy or a halogen atom" is intended to mean that the stated groups have one or more of these groups and atom.

The alkyl in $R^1$ in Ra and Rb has 1 to 10, preferably 1 to 4, carbon atoms. The alkenyl and alkynyl have 2 to 10, preferably 2 to 4, carbon atoms. The fluoroalkyl has 1 to 10, preferably 1 to 4, carbon atoms and 1 to 21, preferably 1 to 9, fluorine atoms, perfluoroalkyl such as trifluoromethyl being especially preferred. The aryls are preferably phenyl or naphthyl and lower alkyl nucleosubstituted phenyl or naphthyl. Preferred aralkyls comprise an aryl moiety of phenyl or lower alkyl nucleosubstituted phenyl and an alkyl moiety of 1 to 4, preferably 1 to 2, carbon atoms.

As mentioned previously, $R^1$ may be any of the above listed groups having the substituent defined earlier. Preferred halogens as substituents are fluorine, chlorine and bromine.

Preferred for Ra is alkyl, alkyl having hydroxy, alkyl having a halogen atom, $-N_3$,

or $-OR^3$ while for Rb is $-N_3$,

or $-OR^3$.

The anthracycline compound of the present invention described above contains basic nitrogen and therefore can form an acid addition salt thereof. Either organic or inorganic acids can be used for the formation of acid addition salts but, when the salts are intended for use as pharmaceutical preparations such as antitumor agents, pharmaceutically acceptable acids should be employed.

Examples of such acids are inorganic acids, e.g., hydrochloric acid, sulfuric acid and phosphoric acid, or organic acids, e.g., acetic acid, propionic acid, maleic acid, oleic acid, palmitic acid, citric acid, succinic acid, tartaric acid, fumaric acid, glutamic acid, pantothenic acid and laurylsulfonic acid.

Typical examples of the anthracycline compound of the formula (I) or (II) according to the present invention include:

(1) 3'-Deamino-3'-[(2"R)-2"-methyl-4"-morpholino]-13-deoxo-10-hydroxycarminomycin (i.e., 3'-deamino-3'-[(2"R)-2"-methyl-4"-morpholino]-R20X2) or an acid addition salt thereof.

(2) 3'-Deamino-3'-[(2"S) -2"-hydroxymethyl-4"-morpholino]-13-deoxo-10-hydroxycarminomycin (i.e., 3'-deamino-3'-[(2"S)-2"-hydroxymethyl-4"-morpholino]-R20X2) or an acid addition salt thereof.

(3) 3'-Deamino-3'-[(2"S)-2"-chloromethyl-4"-morpholino]-13-deoxo-10-hydroxycarminomycin (i.e., 3'-deamino-3'-[(2"S)-2"-chloromethyl-4"-morpholino]-R20X2) or an acid addition salt thereof.

(4) 3'-Deamino-3'-[(2"S)-2"-azido-4"-morpholino]-13-deoxo-10-hydroxycarminomycin (i.e., 3'-deamino-3'-[(2"S)-2"-azido-4"-morpholino]-R20X2) or an acid addition salt thereof.

(5) 3'-Deamino-3'-[(2"S)-2"-acetamido-4"-morpholino]-13-deoxo-10-hydroxycarminomycin (i.e., 3'-deamino-3'-[(2"S)-2"-acetamido-4"-morpholino]-R20X2) or an acid addition salt thereof.

(6) 3'-Deamino-3'-[(2"S)-2"-trifluoroacetamido-4"-morpholino]-13-deoxo-10-hydroxycarminomycin (i.e., 3'-deamino-3'-[(2"S)-2"-trifluoroacetamido-4"-morpholino]-R20X2) or an acid addition salt thereof.

(7) 3'-Deamino-3'-[(2"S)-2"-methoxy-4"-morpholino]-13-deoxo-10-hydroxycarminomycin (i.e., 3'-deamino-3'-[(2"S)-2"methoxy-4"-morpholino]-R20X2) or an acid addition salt thereof.

(8) 3'-Deamino-3'-[(2"R)-2"-azido-4"-morpholino]-13-deoxo-10-hydroxycarminomycin (i.e., 3'-deamino-3'-[(2"R)-2"-azido-4"-morpholino]-R20X2) or an acid addition salt thereof.

(9) 3'-Deamino-3'-[(2"R)-2"-trifluoroacetamido-4"-morpholino]-13-deoxo-10-hydroxycarminomycin (i.e., 3'-deamino-3'-[(2"R)-2"-trifluoroacetamido-4"-morpholino]-R20X2) or an acid addition salt thereof.

(10) 3'-Deamino-3'-[(2"R)-2"-methoxy-4"-morpholino]-13-deoxo-10-hydroxycarminomycin (i.e., 3'-deamino-3'-[(2"R)-2"-methoxy-4"-morpholino]-R20X2) or an acid addition salt thereof.

Production of 3'-deamino-3'-(2"-substituted-4"-morpholino)-anthracycline compound

(1) Outline

The 3'-deamino-3'-(2"-substituted-4"-morpholino)anthracycline compound of the formula (I) or (II) according to the present invention can be produced by any process suitable for the purpose of intramolecularly forming bonds and/or introducing substituents. One instance of such processes comprises chemical modification of R20X2 of the following formula (III) obtained by the cultivation of microorganisms.

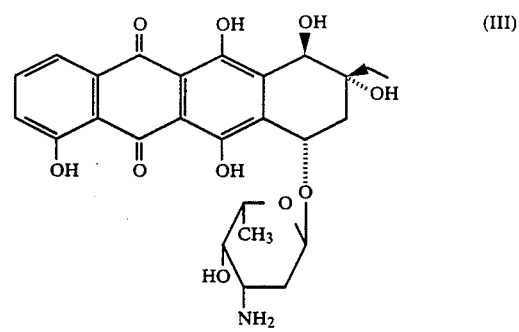

(2) Preparation of R20X2

R20X2 which is the parent compound of the compound of the formula (I) or (II) shown hereinbefore is a known substance and can be prepared by any process suitable for the purpose of intramolecularly forming bonds and/or introducing substituents.

A preferred process for the preparation of R20X2 and its physicochemical properties are described, for example, in Japanese Patent Application Laid-Open Pub. Nos. 167696/1986 and 16495/1987 and U.S. Pat. No. 4,710,564. In the process a specific microorganism, *Actinomadura roseoviolacea* 1029-AV1 (strain R20), is used for the preparation of R20X2. This strain was originally deposited on July 5, 1983 with the Fermentation Research Institute, then assigned, on Dec. 4, 1985, the accession number FERM BP-945 under the terms of the Budapest Treaty and is therefore readily available to the public.

(3) Production of derivatives

As has been set forth earlier, the anthracycline compound of the present invention can be produced by any process suitable for the purpose of intramolecularly forming bonds and/or introducing substituents. In one exemplary process, R20X2 is used as a base compound to produce derivatives, i.e., the anthracycline compounds of the present invention.

The anthracycline compound of the present invention can be obtained by reacting a xylone derivative of any of the following formulae (IV), (V), (VI) and (VII) with sodium metaperiodate, and further reacting the reaction mixture with R20X2 of the formula (II).

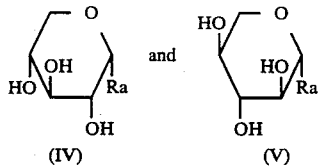

wherein the substituent Ra is as defined previously, and

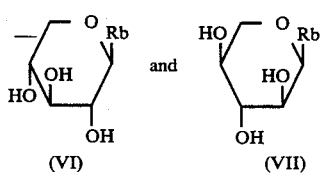

wherein the substituent Rb is as defined previously.

All of the xylose derivatives of the above shown formula (IV), (V), (VI) or (VII) used for the anthracycline compound of the present invention are known compounds or can be prepared by a known synthesis procedure.

The reaction between the reaction mixture obtained by reacting a xylose derivative of the formula (IV), (V), (VI) or (VII) with sodium metaperiodate and R20X2 of the formula (III) is typically carried out in a solvent. Examples of suitable solvents include acetonitrile, methanol, ethanol, water, chloroform, dichloromethane, carbon tetrachloride, benzene, dioxane, and tetrahydrofuran singly or in a mixture, a chloroformmethanol mixture being especially preferred.

Ordinarily, it is preferable that this reaction is conducted in the presence of a reducing agent, for example, sodium borohydride (NaBH$_4$) or sodium cyanoborohydride (NaBH$_3$CN). The amount of the reducing agent used is not critical, and the agent can be used in an amount of at least 1 mol, preferably from 1 to 3 mols, per mol of R20X2.

An appropriate reaction temperature is generally in the range of from the solidifying point of the solvent used to 50°, room temperature being particularly appropriate.

Under the foregoing reaction conditions, the reaction of converting the amino group in R20X2 into 2″-substituted-4″-morpholino group can be terminated within about 10 minutes to 7 hours.

In accordance with the above described process, 3′-deamino-3′-(2″-substituted-4″-morpholino) derivatives can be obtained in crude form through the reaction between the reaction mixture obtained by reacting a xylose derivative of the formula (IV), (V), (VI) or (VII) with sodium metaperiodate and R20X2 of the formula (III). The crude product thus obtained can be purified to isolate the desired compound of the present invention by a known purification procedure utilized in the preparation of anthracyclines or glycoside derivatives thereof. For example, the crude product is extracted with an organic solvent which is immiscible with water, preferably chloroform or methylene chloride. The solvent layer is then concentrated and subjected either to separation based on adsorption such as silica gel column chromatography or thin layer chromatography for isolation or to separation by gel filtration using Sephadex LH20 and the like for purification purposes, whereby the desired substance can be isolated in pure form.

The compound of the formula (I) or (II) according to the present invention can be converted into an acid addition salt thereof, for example, through a treatment with an inorganic acid such as hydrochloric acid, sulfuric acid or phosphoric acid or an organic acid such as acetic acid, propionic acid, maleic acid, oleic acid, palmitic acid, citric acid, succinic acid, tartaric acid, fumaric acid, glutamic acid, pantothenic acid or laurylsulfonic acid following a per se known method.

Utility of the derivatives

The 3′-deamino-3′-(2″-substituted-4″-morpholino)anthracycline compounds of the present invention have carcinostatic activity and thus are useful as medicines.

(1) Physiological activities (1) Anti-proliferative activity against cultivated P388 mouse leukemia cells:

The 3′-deamino-3′-(2″-substituted-4″-morpholino)anthracycline compounds of the present invention possess outstanding anti-proliferative activity against P388 mouse leukemia cells.

More specifically, a medium RPMI 1640 (Rosewell Park Memorial Institute medium 1640) containing a given amount of the 3′-deamino-3′-(2″-substituted-4″-morpholino) anthracycline compound and 10% fetal bovine serum was inoculated with cultivated P388 5×10$^4$ cells/ml. Incubation was carried out at 37° C. in a CO$_2$ incubator, and the number of the cells in each medium was then counted to determine 50% proliferation-inhibitory concentration (IC$_{50}$, ng/ml) relative to the control (no test compounds added). The results obtained are summarized below.

| Compound | IC$_{50}$ (ng/ml) |
|---|---|
| 3′-Deamino-3′-[(2″R)-2″-methyl-4″-morpholino]-R20X2 | 34.0 |
| 3′-Deamino-3′-[(2″S)-2″-hydroxymethyl-4″-morpholino]-R20X2 | 20.0 |
| 3′-Deamino-3′-[(2″S)-2″-chloromethyl-4″-morpholino]-R20X2 | 36.0 |
| 3′-Deamino-3′-[(2″S)-2″-azido-4″- | 24.0 |

-continued

| Compound | IC$_{50}$ (ng/ml) |
|---|---|
| morpholino]-R20X2 | |
| 3'-Deamino-3'-[(2"S)-2"-acetamido-4"-morpholino]-R20X2 | 83.0 |
| 3'-Deamino-3'-[(2"S)-2"-trifluoroacetamide-4"-morpholino]-R20X2 | 52.0 |
| 3'-Deamino-3'-[(2"S)-2"-methoxy-4"-morpholino]-R20X2 | 18.0 |
| 3'-Deamino-3'-[(2"R)-2"-azido-4"-morpholino]-R20X2 | 18.9 |
| 3'-Deamino-3'-[(2"R)-2"-trifluoroacetamido-4"-morpholino]-R20X2 | 22.5 |
| 3'-Deamino-3'-[(2"R)-2"-methoxy-4"-morpholino]-R20X2 | 9.0 |

(2) Antitumor activity:

The 3'-deamino-3'-(2"-substituted-4"-morpholino)anthracycline compounds of the present invention exhibited antitumor activity against experimental tumors in subject animals.

For example, into CDF$_2$ mice were intraperitoneally transplanted P388 leukemia 1×10$^6$ cells/mouse as a suspension, and the 3'-deamino-3'-(2"-substituted-4"-morpholino) anthracycline compounds were administered to the mice intraveneously 1 day and 5 days respectively after the transplantation. The effects of the test anthracycline compounds are shown below in terms of T/C (%), the survival days of the control mice to which physiological saline solutions was administered being specified as 100.

| Compound | Dose (mg/kg) | T/C (%) | Number of cured mice/ Number of test mice |
|---|---|---|---|
| 3'-Deamino-3'-[(2"S)-2"-azido-4"-morpholino]-R20X2 | 0.5 | 122 | 0/6 |
| | 1 | 163 | 0/6 |
| | 2 | 231 | 0/6 |
| | 4 | 355* | 1/6 |
| 3'-Deamino-3'-[(2"S)-2"-acetamido-4"-morpholino]-R20X2 | 2 | 124 | 0/6 |
| | 4 | 124 | 0/6 |
| | 8 | 146 | 0/6 |
| | 16 | 340 | 0/6 |
| 3'-Deamino-3'-[(2"S)-2"-trifluoroacetamido-4"-morpholino]-R20X2 | 2 | 136 | 0/6 |
| | 4 | 181 | 0/6 |
| | 8 | 229 | 0/6 |
| | 16 | 263* | 0/6 |
| 3'-Deamino-3'-[(2"S)-2"-methoxy-4"-morpholino]-R20X2 | 0.125 | 103 | 0/6 |
| | 0.25 | 182 | 0/6 |
| | 0.5 | 196 | 0/6 |
| | 1 | 182* | 0/6 |
| 3'-Deamino-3'-[(2"R)-2"-azido-4"-morpholino]-R20X2 | 0.25 | 115 | 0/6 |
| | 0.5 | 163 | 0/6 |
| | 1 | 196 | 0/6 |
| | 2 | 294 | 0/6 |
| | 4 | 124 | 0/6 |
| 3'-Deamino-3'-[(2"R)-2"-trifluoroacetamido-4"-morpholino]-R20X2 | 2 | 120 | 0/6 |
| | 4 | 150 | 0/6 |
| | 8 | 165 | 0/6 |
| | 16 | 319 | 2/6 |
| 3'-Deamino-3'-[(2"R)-2"-methoxy-4"-morpholino]-R20X2 | 0.125 | 119 | 0/6 |
| | 0.25 | 149 | 0/6 |
| | 0.5 | 172 | 0/6 |
| | 1 | 181 | 0/6 |
| | 2 | 36* | 0/6 |
| 3'Deamino-3'-morpholino-R20X2 | 0.29 | 110 | 0/6 |
| | 0.44 | 143 | 0/6 |
| | 0.66 | 162 | 0/6 |
| | 0.99 | 173 | 0/6 |
| | 1.48 | 189 | 0/6 |
| | 2.22 | 189 | 0/6 |

-continued

| Compound | Dose (mg/kg) | T/C (%) | Number of cured mice/ Number of test mice |
|---|---|---|---|
| | 3.33 | 240 | 0/6 |
| | 5.00 | 135 | 0/6 |

*administered only day 1

(2) Antitumor agent

As has been set forth hereinabove, the 3'-deamino-3'-(2"-substituted-4"-morpholino) anthracycline compounds were found to have antitumor activity against tumors, particularly malignant tumors in subjects Accordingly, the 3'-deamino-3'-(2"-substituted-4"-morpholino) anthracycline compounds of the present invention can be used as antitumor agents or pharmaceutical agents for treating tumors. That is, the antitumor agents according to the, present invention comprise as active ingredients 3'-deamino-3'-(2"-substituted-4"-morpholino) anthracycline compounds of the previously shown formula (I) or (II) or acid addition salts thereof.

The 3'-deamino-3'-(2"-substituted-4"-morpholino) anthracycline compounds as antitumor agents can be administered via any route suited for the desired purpose in a dosage form determined by the route of administration. Ordinarily, the compounds diluted with pharmaceutically acceptable carriers or diluents are administered as drugs.

One of typical methods of administering the 3'-deamino-3'-(2"-substituted-4"-morpholino) anthracycline compounds as antitumor agents is by injection or oral administration of solutions thereof in distilled water for injection use or in physiological saline solution. In clinical applications, the compounds in solution are administered by injection such as intraperitoneal injection, subcutaneous injection, intravenous or intraarterial injection, and topical administration in case of animals; and by intravenous or intraarterial injection, topical administration by injection, and oral administration in case of humans.

The doses of the 3'-deamino-3'-(2"-substituted-4"-morpholino) anthracycline compounds are determined in view of the results of animal experiments and varying circumstances in such a manner that the total of doses given continuously or intermittently in each case will not exceed a predetermined limit. Needless to say, particular doses required may vary depending on the mode of administration; situations of subjects to be treated, such as age, sex, body weight, and susceptibility; food; times of administration; concurrently administered drugs; and conditions of subjects or severity of their diseases. The optimum doses and frequency of administration under certain conditions must be determined by experts' optimum dose determination tests on the basis of the abovementioned parameters. For example, the compound is administered to an adult at a dose of about 0.1 to 1 g/day.

The antitumor agents according to the present invention comprise as active ingredients anthracycline compounds of the formula (I) or (II) or acid addition salts thereof as has been mentioned earlier, and typical examples of the anthracycline compounds are compounds (1) through (10) listed in the paragraph headed 3'-deamino- 3'-(2''-substituted-4''-morpholino) anthracycline compound.

With respect to the type of the anthracycline compound which constitutes the antitumor agent of the present invention, a group of compounds represented by the formula (I), a group of compounds represented by the formula (II), and a group of acid addition salts thereof can be used either singly or in a combination of two or more members selected from within a single group of compounds and/or from among two or more groups of compounds.

EXPERIMENTAL EXAMPLES

In the following examples, "%" is "w/v %".

EXAMPLE 1:

Production of R20X2

(1) Inoculum Preparation

A medium used to grow a primary inoculum was prepared by dissolving the following ingredients in 1 liter of water and adjusting the pH of the resultant solution to 7.2.

| | |
|---|---|
| Polypeptone | 10 g |
| Molasses | 10 g |
| Meat extract | 10 g |

100 ml of the medium thus prepared was sterilized in a 500-ml Erlenmeyer flask and inoculated with a loopful of spores collected from a slant culture of *Actinomadura roseoviolacea* R20. The inoculated medium was subjected to shake culture for 5 days at 27° C. on a rotary shaker (200 r.p.m.) to prepare an inoculum.

(2) Cultivation

A fermentation medium was prepared by dissolving the following ingredients in 1 liter of water and adjusting the pH of the resultant solution to 7.4.

| | |
|---|---|
| Glucose | 25 g |
| Soybean meal | 15 g |
| Dry yeast | 2 g |
| Calcium carbonate (precipitated) | 4 g |

25 liters of the fermentation medium thus prepared was sterilized in a 50-l jar fermenter and inoculated with 3 vials of the inoculums prepared as described above. The fermentation was carried out at 27° C. for 7 days at 1 v.v.m. and 200 r.p.m.

(3) Recovery of R20X2

The fermented mash thus obtained was adjusted to pH 10 and filtered to separate the microorganism cells from the filtrate. The filtrate was adjusted to pH 2, and the precipitate formed was separated by centrifugation and then dried to obtain a dry solid.

The dry solid obtained was dissolved in 1 liter of 2.8% aqueous ammonia. To this solution was added 5 liters of acetone, and the resulting solution was left standing at room temperature for 2 hours and then concentrated.

The residue was extracted three times with chloroform-methanol (10:1). The chloroform-methanol layer was dehydrated over anhydrous sodium sulfate, concentrated, and chromatographed on a column of silica gel using as eluant chloroform-methanol (10:1) to obtain 0.75 g of R20X2.

The supernatant obtained by the centrifugation of the filtrate of the fermented mash, on the other hand, was adsorbed onto "Diaion HP-20" (supplied by Mitsubishi Kasei K.K., Japan) and washed with water. The adsorbate was eluted with 2.8% aqueous ammonia-acetone (1:5). A colored fraction thus eluted was concentrated, and the residue was neutralized with 1N hydrochloric acid and extracted three times with chloroform-methanol (10:1). The chloroform-methanol layer was dehydrated over anhydrous sodium sulfate, concentrated to dryness, and chromatographed on silica gel using as eluant chloroformmethanol (10:1) to obtain 1.35 g of R20X2.

EXAMPLE 2

(1) Synthesis of 3'-deamino-3'-[(2''R)-2''-methyl-4''-morpholino]-R20X2

48.5 mg (0.36 mmol) of 1,5-anhydro-6-deoxy-D-glucitol was dissolved in 5 ml of methanol, and 210 mg (0.98 mmol) of sodium metaperiodate was added. The mixture was stirred at room temperature for 15 hours in the dark. The reaction mixture was then filtered and the filtrate was concentrated under reduced pressure. The residue was dissolved in a mixture of 5 ml each of chloroform and methanol. To the solution were added 77.0 mg (0.15 mmol) of R20X2 and then 18.8 mg (0.30 mmol) of sodium cyanoborohydride, and the mixture was stirred at room temperature for 5 hours. The reaction mixture was then concentrated under reduced pressure and the residue extracted with chloroform (100 ml) and washed with water (80 ml). After washing, the chloroform layer was dehydrated over anhydrous sodium sulfate and concentrated under reduced pressure. The residue was developed on thin-layer chromatography (TLC) (Merck & Co., Inc., No. 5744) using chloroform-methanol (10:1). A band having an Rf value of approximately 0.6 was scraped off and extracted with chloroform-methanol (10:1) to obtain the desired compound which was then crystallized from chloroform-hexane to obtain 20.8 mg (0.035 mmol, 23% yield) of the title compound as a brown powder.

(2) Physicochemical properties of 3'-deamino-3'-[(2''R)-2''-methyl-4''-morpholino]-R20X2

(1) Melting point: 161°–164° C. (decomposed)
(2) $[\alpha]_D^{25} = +140°$ (C=0.06, CHCl$_3$)
(3) Elementary analysis:

| | C | H | N | |
|---|---|---|---|---|
| Calcd. | 62.09 | 6.22 | 2.34 | (C$_{31}$H$_{37}$NO$_{11}$) |
| Found | 61.83 | 6.31 | 2.33 | (%) |

(4) FD-MS m/z=599 (M$^+$)
(5) Infrared absorption spectrum (KBr)(cm$^{-1}$): 3450, 1610
(6) $^1$H-Nuclear magnetic resonance spectrum (500 MHz, in deuterochloroform) (δ (ppm)):

13.63 (1H, s, 11-OH), 12.86 (1H, s, 6-OH), 12.16 (1H, s, 4-OH), 7.91 (1H, dd, J=1.5, 7.3 Hz, H-1), 7.73 (1H, t, J=7.3 Hz, H-2), 7.34 (1H, dd, J=1.5, 7.3 Hz, H-3), 5.52 (1H, brs, H-1'), 5.16 (1H, brs, H-7), 4.92 (1H, brs, H-10), 4.09 (1H, q, J=5.7 Hz, H-5'), 4.00 (1H, s, 9-OH), 3.84 (1H, brd, J=11.0 Hz, H-6''a), 3.70 (1H, brs, H-4'), 3.65-3.50 (2H, H-2'', H-6''b), 2.89 (1H, d, J=11.0 Hz, H-5″a), 2.72-2.64 (2H, H-3″a, 10-OH), 2.38 (1H, m, H-3′), 2.25 (1H, d, J=14.6 Hz, H-8a), 2.12 (1H, dd, J=3.7, 14.6 Hz, H-8b), 2.06 (1H, dt, J=3.0, 11.0 Hz, H-5″b), 1.95-1.74 (5H, H-13, H-2′, H-3″b), 1.40 (3H, d, J=5.7 Hz, H-6′), 1.12 (3H, t, J=7.3 Hz, H-14), 1.09 (3H, d, J=6.1Hz, H-7″)

EXAMPLE 3

(1) Synthesis of 3′-deamino-3′-[(2″S)-2″-hydroxymethyl-4″-morpholino]-R20X2

337.5 mg (2.06 mmol) of 1,5-anhydro-D-glucitol was dissolved in 30 ml of methanol, and 1.32 g (6.17 mmol) of sodium metaperiodate was added. The mixture was allowed to react at room temperature for 21 hours in the dark. The reaction mixture was then filtered and the filtrate concentrated under reduced pressure. The residue was dissolved in a mixture of 5 ml each of chloroform and methanol. To the solution were added 67.9 mg (0.13 mmol) of R20X2 and 85.6 mg (0.40 mmol) of sodium cyanoborohydride, and the mixture was allowed to react for 6 hours. The reaction mixture was then concentrated and the residue extracted with chloroform (200 ml). The chloroform layer was washed with water (200 ml), dehydrated over anhydrous sodium sulfate and concentrated under reduced pressure. The residue was developed on TLC (Merck & Co., Inc., No. 5744) using chloroform-methanol (10:1). A red band having an Rf value of approximately 0.58 was scraped off and extracted with chloroformmethanol (10:1) to obtain the desired compound which was then crystallized from chloroform-hexane (by dissolution in chloroform followed by addition of hexane until the compound was precipitated) to obtain 39.7 mg (0.06 mmol, 50% yield) of the title compound as a brown powder.

(2) Physicochemical properties of 3′-deamino-3′-[(2″S)-2″-hydroxymethyl-4″-morpholino]-R20X2

(1) Melting point: 164.5°-165.5° C. (decomposed)
(2) $[\alpha]_D^{25}=+355°$ (C=0.11, chloroform)
(3) Elementary analysis:

|  | C | H | N |  |
| --- | --- | --- | --- | --- |
| Calcd. | 60.48 | 6.06 | 2.28 | ($C_{31}H_{37}NO_{12}$) |
| Found | 60.26 | 6.12 | 2.25 | (%) |

(4) FD-MS m/z=616 (M+1)
(5) Infrared absorption spectrum (KBr)(cm$^{-1}$): 3400, 1600
(6) $^1$H-Nuclear magnetic resonance spectrum (500 MHz, in deuterochloroform) (δ (ppm)):

13.63 (1H, s, 11-OH), 12.87 (1H, s, 6-OH), 12.15 (1H, s, 4-OH), 7.91 (1H, d, J=7.8 Hz, H-1), 7.73 (1H, t, J=7.8 Hz, H-2), 7.34 (1H, d, J=7.8 Hz, H-3), 5.52 (1H, brs, H-1′), 5.15 (1H, brs, H-7), 4.92 (1H, brs, H-10), 4.09 (1H, q, J=6.6 Hz, H-5′), 3.97 (1H, s, 9-OH), 3.90 (1H, brd, H-6″a), 3.71 (1H, brs, H-4′), 3.65-3.53 (3H, H-6″b, H-7″), 3.50 (1H, dd, J=5.9, 10.9 Hz, H-2″), 2.92 (1H, d, J=10.9 Hz, H-5″a), 2.70 (1H, d, J=10.9 Hz, H-3″a), 2.69 (1H, s, 10-OH), 2.40 (1H, ddd, J=2.5, 6.3, 10.9 Hz, H-3′), 2.26 (1H, d, J=15.3 Hz, H-8a), 2.12 (1H, dd, J=3.8, 15.3 Hz, H-8b), 2.07 (1H, dd, J=3.8, 10.9 Hz, H-5″b), 1.98 (1H, t, J=10.9 Hz, H-3″b), 1.90-1.75 (4H, H-13, H-2′), 1.40 (3H, d, J=6.6 Hz, H-6′), 1.12 (3H, t, J=6.9 Hz, H-14)

EXAMPLE 4

(1) Synthesis of 3′-deamino-3′-[(2″S)-2″-chloromethyl-4″-morpholino]-R20X2

895 mg (3.08 mmol) of 1,5-anhydro-2,3,4-tri-O-acetyl-D-glucitol was dissolved in 30 ml of pyridine, and 1.95 g (7.4 mmol) of triphenylphosphine and 10 ml of carbon tetrachloride were added. The mixture was allowed to react at 45° to 50° C. for 2 hours. The reaction mixture was then concentrated under reduced pressure and the residue extracted with chloroform (80 ml). The chloroform layer was washed with 1N aqueous hydrochloric acid solution (80 ml) and water (80 ml), dehydrated over anhydrous sodium sulfate and concentrated under reduced pressure. The residue was subjected to column chromatography (Waggle C-200, 40 g) and eluted with chloroform-methanol (300:1). The eluate was crystallized from ethyl acetate-hexane to obtain 562 mg (1.82 mmol, 59%) of 1,5-anhydro-6-chloro-6-deoxy-2,3,4-tri-O-acetyl-D-glucitol as a colorless needle crystal. Shown below are physicochemical properties of the crystalline compound thus obtained.

Melting point: 129°-131° C.
$[\alpha]_D^{24}=+38°$ (C=0.3, CHCl$_3$)
FD-MS: m/z=309 (M$^+$+1)
Infrared absorption spectrum (KBr)(cm$^{-1}$): 1730
$^1$H-Nuclear magnetic resonance spectrum (500 MHz, in deuterochloroform) (δ (ppm)):

5.21 (1H, t, J=9.1 Hz, H-3), 5.05-4.98 (2H, H-2, H-4), 4.18 (1H, dd, J=6.3, 11.4 Hz, H-1a), 3.66-3.62 (2H, H-5, H-6a), 3.52 (1H, dd, J=6.3, 11.4 Hz, H-6b), 3.33 (1H, t, J=11.4 Hz, H-1b), 2.06 (3H, s, COCH$_3$), 2.04 (3H, s, COCH$_3$), 2.03 (3H, s, COCH$_3$)

Subsequently, 94 mg (0.30 mmol) of this 1,5-anhydro-6-chloro-6-deoxy-2,3,4-tri-O-acetyl-D-glucitol was dissolved in 5 ml of methanol, and 0.1 ml of sodium methoxide was added. The mixture was allowed to react at 0° C. for 30 minutes, and thereafter neutralized with an acidic ion exchange resin, Amberlite IR-120B. The resin was removed by filtration, and 194 mg (0.91 mmol) of sodium metaperiodate was added to the filtrate. The resultant filtrate was allowed to react at room temperature for 20 hours in the dark. The reaction solution was then filtered and the filtrate concentrated under reduced pressure. The residue was dissolved in a mixture of 5 ml each of chloroform and methanol. To the solution were added 51.6 mg (0.10 mmol) of R20X2 and then 18.9 mg (0.30 mmol) of sodium cyanoborohydride, and the mixture was allowed to react at room temperature for 4 hours. The reaction mixture was then concentrated to dryness and the residue extracted with chloroform (100 ml). The chloroform layer was washed with water (100 ml), dehydrated over anhydrous sodium sulfate and concentrated under reduced pressure. The residue was developed on TLC (Merck & Co., Inc., No. 5744) using chloroform-methanol (10:1). A red band having an Rf value of approximately 0.62 was scraped off and extracted with chloroform-methanol (10:1) to obtain the desired compound which was then crystallized from chloroformhexane to obtain 28.2 mg (0.04 mmol, 44% yield) of the title compound as a brown powder.

(2) Physicochemical properties of 3'-deamino-3'-[(2''S)-2''-chloromethyl-4''-morpholino]-R20X2

(1) Melting point: 148°–150° C. (decomposed)
(2) $[\alpha]_D^{24} = +60°$ (C=0.09, CHCl$_3$)
(3) Elementary analysis:

|  | C | H | N |  |
| --- | --- | --- | --- | --- |
| Calcd. | 58.72 | 5.72 | 2.21 | (C$_{31}$H$_{36}$NO$_{11}$Cl) |
| Found | 58.49 | 5.79 | 2.19 | (%) |

(4) FD-MS m/z=634 (M+)
(5) Infrared absorption spectrum (KBr)(cm$^{-1}$): 3420, 1600
(6) $^1$H-Nuclear magnetic resonance spectrum (500 MHz, in deuterochloroform) (δ (ppm)):
13.63 (1H, s, 11-OH), 12.87 (1H, s, 6-OH), 12.16 (1H, s, 4-OH), 7.90 (1H, d, J=8.1Hz, H-1), 7.73 (1H, t, J=8.1 Hz, H-2), 7.34 (1H, d, J=8.1 Hz, H-3), 5.53 (1H, brs, H-1'), 5.17 (1H, brs, H-7), 4.92 (1H, s, H-10), 4.10 (1H, q, J=6.6 Hz, H-5'), 3.98 (1H, s, 9-OH), 3.92 (1H, d, J=12.2 Hz, H-6''a), 3.72 (1H, brs, H-4'), 3.68 (1H, m, H-2''), 3.62 (1H, dt, J=3.1, 12.2 Hz, H-6''b), 3.49 (1H, dd, J=4.7, 11.6 Hz, H-7''a), 3.43 (1H, dd, J=5.9, 11.6 Hz, H-7''b), 2.89 (2H, H-3''a, H-5''a), 2.69 (1H, s, 10-OH), 2.44 (1H, m, H-3'), 2.25 (1H, d, J=15.6 Hz, H-8a), 2.16-2.09 (2H, H-8b, H-5''b), 1.97 (1H, t, J=10.0 Hz, H-3''b), 1.90-1.74 (4H, H-13, H-2'), 1.41 (3H, d, J=6.6 Hz, H-6'), 1.13 (3H, t, J=7.8 Hz, H-14)

EXAMPLE 5

(1) Synthesis of 3'-deamino-3'-[(2''S)-2''-azido-4''-morpholino]-R20X2

4.88 g (12.2 mmol) of 2,3,4-tri-O-acetyl-α-L-xylopyranosyl bromide was dissolved in 40 ml of N,N-dimethylformamide, and 4.5 g (69.2 mmol) of sodium azide was added. The mixture was allowed to react at room temperature for 18 hours. The reaction mixture was then concentrated under reduced pressure and the residue extracted with chloroform (250 ml). The chloroform layer was washed with water (250 ml), dehydrated over anhydrous sodium sulfate and concentrated under reduced pressure. The residue was subjected to column chromatography (Waggle C-200, 40 g) and eluted with chloroform-methanol (100:1). The eluate was crystallized from ethyl acetate-hexane to obtain 2.95 g (9.79 mmol, 68%) of 2,3,4-tri-O-acetyl-β-L-xylopyranosyl azide as a colorless needle crystal. The following are the physicochemical properties of this crystalline compound.

Melting point: 83° C.
$[\alpha]_D^{24} = 30\ 119°$ (C=1.0, chloroform)
Infrared absorption spectrum (KBr)(cm$^{-1}$): 2130, 1750
FD-MS: m/z=302 (M+ +1)
$^1$H-Nuclear magnetic resonance spectrum (500 MHz, in deuterochloroform) (δ(ppm)):
5.20 (1H, t, J=9.0 Hz, H-3), 4.98 (1H, ddd, J=5.0, 9.0, 10.0 Hz, H-4), 4.88 (1H, t, J=9.0 Hz, H-2), 4.64 (1H, d, J=9.0 Hz, H-1), 4.22 (1H, dd, J=5.0, 13.0 Hz, H-5a), 3.44 (1H, dd, J=10.0, 13.0 Hz, H-5b), 2.08 (3H, s, COCH$_3$), 2.05 (3H, s, COCH$_3$), 2.04 (3H, s, COCH$_3$)

Subsequently, 309.0 mg (1.03 mmol) of the 2,3,4-tri-O-acetyl-β-L-xylopyranosyl azide was dissolved in 5 ml of methanol, and 0.1 ml of sodium methoxide was added. The mixture was stirred at room temperature for 3 hours, and thereafter the reaction solution was neutralized with an acidic ion exchange resin, Amberlite IR-120B. The resin was removed by filtration, and 517.7 mg (2.42 mmol) of sodium metaperiodate was added to the filtrate. The resultant filtrate was allowed to react at room temperature for 22 hours in the dark. The reaction solution was then filtered and the filtrate concentrated under reduced pressure. The residue was dissolved in 10 ml each of chloroform and methanol. To the solution were added 130.0 mg (0.25 mmol) of R20X2 and 47.5 mg (0.76 mmol) of sodium cyanoborohydride, and the mixture was stirred at room temperature for 6 hours. The reaction mixture was then concentrated under reduced pressure and the residue extracted with chloroform (150 ml). The chloroform layer was washed with water (150 ml), dehydrated over anhydrous sodium sulfate and concentrated under reduced pressure. The residue was developed on TLC (Merck & Co., Inc., No. 5744) using chloroform-methanol (15:1). A red band having an Rf value of approximately 0.48 was scraped off and extracted with chloroform methanol (10:1) to obtain the desired compound which was then crystallized from chloroform-hexane to obtain 60.8 mg (0.10 mmol, 38% yield) of the title compound as a brown powder.

(2) Physicochemical properties of 3'-deamino-3'-[(2''S)-2''-azido-4''-morpholino]-R20X2

(1) Melting point: 138°–139° C. (decomposed)
(2) $[\alpha]_D^{24} = +78°$ (C=0.11, CHCl$_3$)
(3) Elementary analysis:

|  | C | H | N |  |
| --- | --- | --- | --- | --- |
| Calcd. | 57.50 | 5.47 | 8.94 | (C$_{30}$H$_{34}$N$_4$O$_{11}$) |
| Found | 57.63 | 5.22 | 8.70 | (%) |

(4) FD-MS 627 (M+ +1)
(5) Infrared absorption spectrum (KBr)(cm$^{-1}$): 3450, 2100, 1600
(6) $^1$H-Nuclear magnetic resonance spectrum (500 MHz, in deuterochloroform) (δ (ppm)):
13.62 (1H, s, 11-OH), 12.85 (1H, s, 6-OH), 12.14 (1H, s, 4-OH), 7.90 (1H, d, J=7.4 Hz, H-1), 7.73 (1H, t, J=7.4 Hz, H-2), 7.33 (1H, d, J=7.4 Hz, H-3), 5.51 (1H, s, H-1'), 5.15 (1H, s, H-7), 4.97 (1H, brs, H-2''), 4.92 (1H, s, H-10), 4.08 (1H, q, J=6.5 Hz, H-5'), 4.01 (1H, m, H-6''a), 3.94 (1H, s, 9-OH), 3.71-3.64 (2H, H-4', H-6''b), 2.62-2.3-5 (5H, H-3', H-3'', H-5''), 2.25 (1H, d, J=14.3 Hz, H-8a), 2.12 (1H, dd, J=4.2, 14.3 Hz, H-8b), 1.90-1.73 (4H, H-13, H-2'), 1.40 (3H, d, J=6.5 Hz, H-6'), 1.12 (3H, t, J=7.4 Hz, H-14)

EXAMPLE 6

(1) Synthesis of 3'-deamino-3'-[(2''S)-2''-acetamido-4''-morpholino]-R20X2

997.2 mg (3.31 mmol) of 2,3,4-tri-O-acetyl-β-L-xylopyranosyl azide was dissolved in 30 ml of methanol, and the solution was allowed to react at 45° to 50° C. for 2 hours in a hydrogen gas stream in the presence of 300 mg of 5% palladium carbon catalyst. The reaction solution was then filtered and the filtrate concentrated under reduced pressure. The residue was dissolved in 60 ml of pyridine, and 10 ml of acetic anhydride was added. The mixture was allowed to react at room temperature for 4 hours. The reaction mixture was then concentrated under reduced pressure and the residue extracted with chloroform (100 ml). The chloroform layer was washed with 2N aqueous hydrochloric acid solution (100 ml), 10% aqueous sodium carbonate solution (100 ml) and water in the stated order, dehydrated over anhydrous sodium sulfate and concentrated under reduced pressure. The residue was subjected to column chromatography (Waggle C-200, 30 g) and eluted with chloroform-methanol (300:1). The eluate was crystallized from ethyl acetate-hexane to obtain 309.9 mg (0.98 mmol, 30%) of 2,3,4-tri-O-acetyl-$\beta$-L-xylopyranosylamine as a colorless needle crystal. The physicochemical properties of this crystalline compound were as follows.

Melting point: 148°–149° C.

$[\alpha]_D^{24} = -24°$ (C=1.0, methanol)

Infrared absorption spectrum (KBr)(cm$^{-1}$): 1760, 1740, 1660

FD-MS m/z=317 (M+)

$^1$H-Nuclear magnetic resonance spectrum (500 MHz, in deuterochloroform) ($\delta$ (ppm)):

6.48 (1H, d, J=10.0 Hz, NH), 5.30 (1H, t, J=10.0 Hz, H-1), 5.17 (1H, t, J=10.0 Hz, H-3), 4.98 (1H, ddd, J=5.5, 10.0, 11.0 Hz, H-4), 4.88 (1H, t, J=10.0 Hz, H-2), 4.07 (1H, dd, J=5.5, 11.0 Hz, H-5a), 3.45 (1H, t, J=11.0 Hz, H-5b), 2.07 (3H, s, OCOCH$_3$), 2.05 (3H, s, OCOCH$_3$), 2.04 (3H, s, OCOCH$_3$), 2.00 (3H, s, NHCOCH$_3$)

309.9 mg (0.98 mmol) of this N-acetyl-2,3,4-tri-O-acetyl-$\beta$-L-xylopyranosylamine was then dissolved in 30 ml of methanol, and 0.1 ml of sodium methoxide was added. The mixture was stirred at room temperature for 2 hours, and thereafter neutralized with an acidic ion exchange resin, Amberlite IR-120B. The resin was removed by filtration, and 626.7 mg (2.93 mmol) of sodium metaperiodate was added to the filtrate. The resultant filtrate was allowed to react at room temperature for 18 hours in the dark. The reaction solution was then filtered and the filtrate concentrated under reduced pressure. The residue was dissolved in a mixture of 10 ml each of chloroform and methanol. To the solution were added 150 mg (0.29 mmol) of R20X2 and 91.4 mg (1.45 mmol) of sodium cyanoborohydride, and the mixture was allowed to react at room temperature for 6 hours. The reaction mixture was then concentrated under reduced pressure and the residue extracted with chloroform (150 ml). The chloroform layer was washed with water (150 ml), dehydrated over anhydrous sodium sulfate and concentrated under reduced pressure. The residue was developed on TLC (Merck & Co., Inc., No. 5744) using chloroform-methanol (10:1). A red band having an Rf value of approximately 0.58 was scraped off and extracted with chloroformmethanol (10:1) to obtain the desired compound which was then crystallized from chloroform-hexane to obtain 113.9 mg (0.177 mmol, 61% yield) of the title compound as a brown powder.

(2) Physicochemical properties of 3'-deamino-3'-[(2"S)-2"-acetamide-4"-morpholino]-R20X2

(1) Melting point: 173°–174° C. (decomposed)
(2) $[\alpha]_D^{24} = +58°$ (C=0.08, CHCl$_3$)
(3) Elementary analysis:

| | C | H | N | |
|---|---|---|---|---|
| Calcd. | 59.81 | 5.96 | 4.36 | (C$_{32}$H$_{38}$N$_2$O$_{12}$) |

-continued

| | C | H | N | |
|---|---|---|---|---|
| Found | 59.95 | 5.87 | 4.21 | (%) |

(4) FD-MS 643 (M+ +1)

(5) Infrared absorption spectrum (KBr)(cm$^{-1}$): 3420, 1660, 1600

(6) $^1$H-Nuclear magnetic resonance spectrum (500 MHz, in deuterochloroform) ($\delta$ (ppm)):

13.63 (1H, s, 11-OH), 12.85 (1H, s, 6-OH), 12.15 (1H, s, 4-OH), 7.90 (1H, d, J=7.3 Hz, H-1), 7.74 (1H, t, J=7.3 Hz, H-2), 7.35 (1H, d, J=7.3 Hz, H-3), 6.03 (1H, brs, NH), 5.52 (1H, s, H-1'), 5.31 (1H, brs, H-2"), 5.15 (1H, s, H-7), 4.92 (1H, s, H-10), 4.09 (1H, q, J=6.3 Hz, H-5'), 3.93 (1H, s, 9-OH), 3.86 (1H, m, H-6"a), 3.70 (1H, s, H-4'), 3.67 (1H, m, H-6"b), 2.83–2.69 (3H, 10-OH, H-3"a, H-5"a), 2.45 (1H, m, H-3'), 2.35–2.10 (4H, H-8, H-3"b, H-5"b), 1.98 (3H, s, COCH$_3$), 1.91–1.72 (4H, H-13, H-2'), 1.39 (3H, d, J=6.3 Hz, H-6'), 1.12 (3H, t, J=7.8 Hz, H-14)

EXAMPLE 7

(1) Synthesis of 3'-deam ino -3'-[( 2"S) - 2"-trifluoroacetamido-4"-morpholino]-R20X2

1.13 g (3.76 mmol) of 2,3,4-tri-O-acetyl-$\beta$-L-xylopyranosyl azide was dissolved in 30 ml of methanol, and the solution was stirred at 45° to 50° C. for 2 hours in a hydrogen gas stream in the presence of 300 mg of 5% palladium carbon catalyst. The reaction solution was then filtered and the filtrate concentrated under reduced pressure. The residue was dissolved in pyridine (20 ml), and 2 ml of trifluoroacetic anhydride was added. The mixture was allowed to react at room temperature for 1.5 hours. The reaction mixture was then concentrated under reduced pressure and the residue extracted with chloroform (250 ml). The chloroform layer was washed with 2N aqueous hydrochloric acid solution (250 ml), 5% aqueous sodium carbonate solution (250 ml) and water (200 ml) in the stated order, dehydrated over anhydrous sodium sulfate and concentrated under reduced pressure. The residue was subjected to column chromatography (Wakogel C-200, 20 g) and eluted with chloroform-methanol (300:1). The eluate was crystallized from ethyl acetate-hexane to obtain 411.7 mg (1.11 mmol, 29%) of N-trifluoroacetamido-2,3,4-tri-O-acetyl-$\beta$-L-xylopyranosylamine as a colorless needle crystal. Presented below are the physicochemical properties of this crystalline compound.

Melting point: 106° C.

$[\alpha]_D^{24} = -38°$ (C=1.0, chloroform)

Infrared absorption spectrum (KBr)(cm$^{-1}$): 1730, 1560

FD-MS m/z=372 (M+ +1)

$^1$H-Nuclear magnetic resonance spectrum (500 MHz, in deuterochloroform) ($\delta$ (ppm)):

7.28 (1H, d, J=8.5 Hz, NH), 5.34 (1H, t, J=9.2 Hz, H-3), 5.15 (1H, dd, J=8.5, 9.2 Hz, H-1), 5.01 (1H, dt, J=5.5, 9.2 Hz, H-4), 4.98 (1H, t, J=9.2 Hz, H-2), 4.13 (1H, dd, J=5.5, 11.6 Hz, H-5a), 3.46 (1H, dd, J=9.2, 11.6 Hz, H-5b), 2.07 (6H, s, 2XOCOCH$_3$), 2.05 (3H, s, OCOCH$_3$)

Subsequently, 331.0 mg (0.89 mmol) of this N-trifluoroacetamido-2,3,4-tri-O-acety-$\beta$-L-xylopyranosylamine was dissolved in 10 ml of methanol, and 0.1 ml of sodium methoxide was added. The mixture was allowed to react at room temperature for 1 hour, and thereafter neutralized with an acidic ion exchange resin, Amberlite IR-120B. The resin was removed by filtration, and 578 mg (2.70 mmol) of sodium metaperiodate was added to the filtrate. The resultant filtrate was allowed to react at room temperature for 4 hours in the dark. The reaction solution was then filtered and the filtrate concentrated under reduced pressure. The residue was dissolved in 5 ml each of chloroform and methanol. To the solution were added 93.3 mg (0.18 mmol) of R20X2 and 43.1 mg (0.69 mmol) of sodium cyanoborohydride, and the mixture was allowed to react at room temperature for 4 hours. The reaction mixture was then concentrated under reduced pressure and the residue extracted with chloroform (150 ml). The chloroform layer was washed with water (100 ml), dehydrated over anhydrous sodium sulfate and concentrated under reduced pressure. The residue was developed on TLC (Merck & Co., Inc., No. 5744) using chloroform-methanol (10:1). A red band having an Rf value of approximately 0.60 was scraped off and extracted with chloroform-methanol (10:1) to obtain the desired compound which was then crystallized from chloroform-hexane to obtain 25.6 mg (0.04 mmol, 20% yield) of the title compound as a brown powder.

(2) Physicochemical properties of 3'-deamino-3'-[(2"S)-2"-trifluoroacetamide-4"-morpholino]-R20X2

(1) Melting point: 153°–154° C. (decomposed)
(2) $[\alpha]_D^{24} = -18°$ (C=0.16, CHCl$_3$)
(3) Elementary analysis:

|  | C | H | N |  |
|---|---|---|---|---|
| Calcd. | 55.17 | 5.06 | 4.02 | (C$_{32}$H$_{35}$N$_2$O$_{12}$F$_3$) |
| Found | 55.32 | 5.00 | 3.88 | (%) |

(4) FD-MS 697 (M$^+$+1)
(5) Infrared absorption spectrum (KBr)(cm$^{-1}$): 3450, 1730, 1600
(6) $^1$H-Nuclear magnetic resonance spectrum (500 MHz, in deuterochloroform) ($\delta$ (ppm)):

13.64 (1H, s, 11-OH), 12.88 (1H, s, 6-OH), 12.16 (1H, s, 4-OH), 7.91 (1H, d, J=7.3 Hz, H-1), 7.74 (1H, t, J=7.3 Hz, H-2), 7.35 (1H, d, J=7.3 Hz, H-3), 7.03 (1H, brs, NH), 5.54 (1H, s, H-1'), 5.36 (1H, m, H-2"), 5.16 (1H, s, H-7), 4.92 (1H, d, J=4.3 Hz, H-10), 4.11 (1H, q, J=6.9 Hz, H-5'), 3.92 (1H, s, 9-OH), 3.87 (1H, m, H-6"a), 3.72 (1H, s, H-4'), 3.70 (1H, m, H-6"b), 2.82 (1H, d, J=10.6 Hz, H-3"a), 2.70 (1H, m, H-5"a), 2.68 (1H, d, J=4.3 Hz, 10-OH), 2.49 (1H, m, H-3'), 2.45–2.28 (2H, H-3"b, H-5"b), 2.23 (1H, d, J=15.1Hz, H-8a), 2.14 (1H, dd, J=4.6, 15.1Hz, H-8b), 1.91–1.73 (4H, H-13, H-2'), 1.38 (3H, d, J=6.9 Hz, H-6'), 1.12 (3H, t, J=7.4 Hz, H-14)

EXAMPLE 8

(1) Synthesis of 3'-deamino-3'-[(2"S)-2"methoxy-4"-morpholino]-R20X2

150 mg (0.91 mmol) of methyl-α-D-xylopyranoside was dissolved in 30 ml of methanol, and 590 mg (2.76 mmol) of sodium metaperiodate was added. The mixture was allowed to react at room temperature for 14 hours in the dark. The reaction mixture was then filtered and the filtrate concentrated under reduced pressure. The residue was dissolved in 5 ml each of chloroform and methanol. To the solution were added 134 mg (0.26 mmol) of R20X2 and 50.3 mg (0.80 mmol) of sodium cyanoborohydride, and the mixture was allowed to react at room temperature for 16 hours. The reaction mixture was then concentrated under reduced pressure and the residue extracted with chloroform (100 ml). The chloroform layer was washed with water (100 ml), dehydrated over anhydrous sodium sulfate and concentrated under reduced pressure. The residue was developed on TLC (Merck & Co., Inc., No. 5744) using chloroform-methanol (10:1). A red band having an Rf value of approximately 0.5 was scraped off and extracted with chloroform-methanol (10:1) to obtain the desired compound which was then crystallized from chloroform-hexane to obtain 88.0 mg (0.14 mmol, 54% yield) of the title compound as a brown powder.

(2) Physicochemical properties of 3'-deamino-3'-[(2"S)-2"-methoxy-4"-morpholino]-R20X2

(1) Melting point: 150°–151° C. (decomposed)
(2) $[\alpha]_D^{24} = +53°$ (C=0.06, CHCl$_3$)
(3) Elementary analysis:

|  | C | H | N |  |
|---|---|---|---|---|
| Calcd. | 60.48 | 6.06 | 2.28 | (C$_{31}$H$_{37}$NO$_{12}$) |
| Found | 60.71 | 5.91 | 2.04 | (%) |

(4) FD-MS 616 (M$^+$+1)
(5) Infrared absorption spectrum (KBr)(cm$^{-1}$): 3420, 1600
(6) $^1$H-Nuclear magnetic resonance spectrum (500 MHz, in deuterochloroform) ($\delta$ (ppm)):

13.61 (1H, s, 11-OH), 12.83 (1H, s, 6-OH), 12.13 (1H, s, 4-OH), 7.88 (1H, d, J=7.9 Hz, H-1), 7.72 (1H, t, J=7.9 Hz, H-2), 7.33 (1H, d, J=7.9 Hz, H-3), 5.50 (1H, s, H-1'), 5.14 (1H, brs, H-7), 4.91 (1H, s, H-10), 4.48 (1H, dd, J=3.2, 4.3 Hz, H-2"), 4.08 (1H, q, J=7.2 Hz, H-5'), 3.97 (1H, s, 9-OH), 3.92 (1H, ddd, J=3.0, 7.2, 11.8 Hz, H-6"a), 3.67 (1H, brs, H-4'), 3.54 (1H, ddd, J=3.3, 6.3, 11.8 Hz, H-6"b), 3.38 (3H, s, OCH$_3$), 2.57–2.36 (5H, H-3', H-3", H-5"), 2.25 (1H, d, J=15.5 Hz, H-8a), 2.12 (1H, dd, J=3.9, 15.5 Hz, H-8b), 1.90–1.73 (4H, H-13, H-2'), 1.39 (3H, d, J=7.2 Hz, H-6'), 1.12 (3H, t, J=7.2 Hz, H-14)

EXAMPLE 9

(1) Synthesis of 3'-deamino-3'-[(2"R)-2"-azido-4"-morpholino]-R20X2

249.5 mg (1.42 mmol) of β-D-xylopyranosyl azide was dissolved in 10 ml of methanol, and 914.3 mg (4.27 mmol) of sodium metaperiodate was added. The mixture was allowed to react at room temperature for 19 hours in the dark. The reaction mixture was then concentrated under reduced pressure and the residue dissolved in 10 ml of methanol. To the solution were added 60.0 mg (0.12 mmol) of R20X2 and 21.9 mg (0.10 mmol) of sodium cyanoborohydride, and the mixture was allowed to react at room temperature for 2 hours. The reaction mixture was thereafter concentrated under reduced pressure and the residue extracted with chloroform (100 ml). The chloroform layer was washed with water (100 ml), dehydrated over anhydrous sodium sulfate and concentrated under reduced pressure. The residue was developed on TLC (Merck & Co., Inc., No. 5744) using chloroform-methanol (10:1). A red band having an Rf value of approximately 0.65 was scraped off and extracted with chloroform-methanol (10:1) to obtain the desired compound which was then crystallized from chloroform-hexane to obtain 27.1 mg (0.04 mmol, 37% yield) of the title compound as a brown powder.

(2) Physicochemical properties of 3'-deamino-3'-[(2"R)-2"-azido-4"-morpholino]-R20X2

(1) Melting point: 150°–152° C. (decomposed)
(2) $[\alpha]_D^{24} = +122°$ (C=0.07, CHCl$_3$)
(3) Elementary analysis:

|  | C | H | N |  |
| --- | --- | --- | --- | --- |
| Calcd. | 57.50 | 5.47 | 8.94 | (C$_{30}$H$_{34}$N$_4$O$_{11}$) |
| Found | 57.78 | 5.33 | 8.68 | (%) |

(4) FD-MS m/z=627 (M+1$^+$)
(5) Infrared absorption spectrum (KBr)(cm$^{-1}$): 3430, 2100, 1600
(6) $^1$H-Nuclear magnetic resonance spectrum (500 MHz, in deuterochloroform) (δ (ppm)):
13.62 (1H, s, 11-OH), 12.85 (1H, s, 6-OH), 12.15 (1H, s, 4-OH), 7.91 (1H, d, J=8.1Hz, H-1), 7.73 (1H, t, J=8.1Hz, H-2), 7.34 (1H, d, J=8.1 Hz, H-3), 5.52 (1H, brs, H-1'), 5.15 (1H, brs, H-7), 4.92 (2H, H-10, H-2"), 4.08 (1H, q, J=6.3 Hz, H-5'), 4.00 (1H, m, H-6'a), 3.92 (1H, s, 9-OH), 3.69 (1H, brs, H-4'), 3.67 (1H, m, H-6"b), 2.70–2.40 (4H, H-3", H-5"), 2.37 (1H, dd, J=5.0, 11.9 Hz, H-3'), 2.24 (1H, d, J=15.6 Hz, H-8a), 2.13 (1H, dd, J=4.4, 15.6 Hz, H-8b), 1.90–1.73 (4H, H-13, H-2'), 1.40 (3H, d, J=6.3 Hz, H-6'), 1.12 (3H, t, J=7.5 Hz, H-14)

EXAMPLE 10

(1) Synthesis of 3'-deamino-3'-[(2"R)-2"-trifluoroacetamido-4"-morpholino]-R20X2

188.2 mg (0.76 mmol) of N-trifluoroacetyl-β-D-xylopyranosylamine was dissolved in 10 ml of methanol, and 493 mg (2.30 mmol) of sodium metaperiodate was added. The mixture was allowed to react at room temperature for 18 hours in the dark. The reaction mixture was then filtered and the filtrate concentrated under reduced pressure. The residue was dissolved in 5 ml each of chloroform and methanol. To the solution were added 241.1 mg (0.47 mmol) of R20X2 and 43.9 mg (0.70 mmol) of sodium cyanoborohydride, and the mixture was allowed to react at room temperature for 3 hours. The reaction mixture was then concentrated under reduced pressure and the residue extracted with chloroform (400 ml). The chloroform layer was washed with water (400 ml), dehydrated over anhydrous sodium sulfate and concentrated under reduced pressure. The residue was developed on TLC (Merck & Co., Inc., No. 5744) using chloroform-methanol (10:1). A red band having an Rf value of approximately 0.62 was scraped off and extracted with chloroform-methanol (10:1) to obtain the desired compound which was then crystallized from chloroform-hexane to obtain 78.5 mg (0.11 mmol, 24% yield) of the title compound as a brown powder.

(2) Physicochemical properties of 3'-deamino-3'-[(2"R)-2"-trifluoroacetamido-4"-morpholino]-R20X2

(1) Melting point: 170°–171° C. (decomposed)
(2) $[\alpha]_D^{25} = +189°$ (C=0.11, chloroform)

(3) Elementary analysis:

|  | C | H | N |  |
| --- | --- | --- | --- | --- |
| Calcd. | 55.17 | 5.06 | 4.02 | (C$_{32}$H$_{35}$N$_2$O$_{12}$F$_3$) |
| Found | 54.88 | 5.18 | 3.97 | (%) |

(4) FD-MS m/z=697 (M+1$^+$)
(5) Infrared absorption spectrum (KBr)(cm$^{-1}$): 3450, 1730, 1610
(6) $^1$H-Nuclear magnetic resonance spectrum (500 MHz, in deuterochloroform) (δ (ppm)):
13.63 (1H, s, 11-OH), 12.87 (1H, s, 6-OH), 12.15 (1H, s, 4-OH), 7.92 (1H, d, J=8.9 Hz, H-1), 7.74 (1H, t, J=8.9 Hz, H-2), 7.34 (1H, d, J=8.9 Hz, H-3), 7.04 (1H, d, J=6.9 Hz, NH), 5.53 (1H, d, J=3.4 Hz, H-1'), 5.37 (1H, m, H-2"), 5.15 (1H, brs, H-7), 4.92 (1H, d, J=4.3 Hz, H-10), 4.12 (1H, q, J=5.7 Hz, H-5'), 3.89 (1H, s, 9-OH), 3.84 (1H, dt, J=5.7, 11.7 Hz, H-6"a), 3.74 (1H, brs, H-4'), 3.70 (1H, dt, J=5.1, 11.7 Hz, H-6"b), 2.87 (1H, dd, J=2.3, 11.7 Hz, H-3"a), 2.67 (1H, d, J=4.3 Hz, 10-OH), 2.55 (2H, H-5"), 2.48 (1H, ddd, J=2.3, 4.9, 11.7 Hz, H-3"b), 2.42 (1H, dd, J=5.1, 12.0 Hz, H-3'), 2.32 (1H, d, J=2.3 Hz, 4'-OH), 2.23 (1H, d, J=14.6 Hz, H-8a), 2.13 (1H, dd, J=4.9, 14.6 Hz, H-8b), 1.95–1.70 (4H, H-13, H-2'), 1.38 (3H, d, J=5.7 Hz, H-6'), 1.12 (3H, t, J=7.1Hz, H-14)

EXAMPLE 11

(1) Synthesis of 3'-deamino-3'-[(2"R)-2"-methoxy-4"-morpholino]-R20X2

500 mg (3.05 mmol) of methyl-β-D-xylopyranoside was dissolved in 10 ml of methanol, and 1.95 g (9.12 mmol) of sodium metaperiodate was added. The mixture was allowed to react at room temperature for 23 hours in the dark. The reaction mixture was then filtered and the filtrate concentrated under reduced pressure. The residue was dissolved in 5 ml each of chloroform and methanol. To the solution were added 130 mg (0.25 mmol) of R20X2 and 143 mg (0.67 mmol) of sodium cyanoborohydride, and the mixture was allowed to react at room temperature for 3 hours. The reaction mixture was then concentrated under reduced pressure and the residue extracted with chloroform (200 ml). The chloroform layer was washed with water (200 ml), dehydrated over anhydrous sodium sulfate and concentrated under reduced pressure The residue was developed on TLC (Merck & Co., Inc., No. 5744) using chloroform-methanol (10:1). A red band having an Rf value of approximately 0.53 was scraped off and extracted with chloroform-methanol (10:1) to obtain the desired compound which was then crystallized from chloroform-hexane to obtain 59.9 mg (0.10 mmol, 39% yield) of the title compound as a brown powder.

(2) Physicochemical properties of 3'-deamino-3'-[(2"R)-2"-methoxy-4"-morpholino]-R20X2

(1) Melting point: 147°–148° C. (decomposed)
(2) $[\alpha]_D^{24} = +150°$ (C=0.10, CHCl$_3$)
(3) Elementary analysis:

|  | C | H | N |  |
| --- | --- | --- | --- | --- |
| Calcd. | 60.48 | 6.06 | 2.28 | (C$_{31}$H$_{37}$NO$_{12}$) |

-continued

| | C | H | N |
|---|---|---|---|
| Found | 60.66 | 6.01 | 2.05 (%) |

(4) FD-MS m/z=615 (M+)

(5) Infrared absorption spectrum (KBr)(cm$^{-1}$): 3420, 1600

(6) $^1$H-Nuclear magnetic resonance spectrum (500 MHz, in deuterochloroform) (δ (ppm)):

13.63 (1H, s, 11-OH), 12.85 (1H, s, 6-OH), 12.16 (1H, s, 4-OH), 7.90 (1H, d, J=7.2 Hz, H-1), 7.73 (1H, t, J=7.2 Hz, H-2), 7.34 (1H, d, J=7.2 Hz, H-3), 5.51 (1H, s, H-1'), 5.15 (1H, s, H-7), 4.92 (1H, d, J=3.6 Hz, H-10), 4.45 (1H, dd, J=2.3, 4.9 Hz, H-2''), 4.07 (1H, q, J=6.6 Hz, H-5'), 3.97 (1H, s, 9-OH), 3.92 (1H, ddd, J=3.0, 6.9, 11.8 Hz, H-6''a), 3.70 (1H, s, H-4'), 3.56 (1H, ddd, J=3.3, 6.3, 11.8 Hz, H-6''b), 3.40 (3H, s, OCH$_3$), 2.67 (1H, d, J=3.6 Hz, 10-OH), 2.63 (1H, dd, J=2.3, 11.8 Hz, H-3''a), 2.55 (1H, m, H-5''a), 2.42–2.36 (3H, H-3', H-3''b, H-5''b), 2.25 (1H, d, J=14.1 Hz, H-8a), 2.12 (1H, dd, J=4.6, 14.1 Hz, H-8b), 1.90–1.75 (4H, H-13, H-2'), 1.40 (3H, d, J=6.6 Hz, H-6'), 1.12 (3H, t, J=7.2 Hz, H-14)

We claim:

1. An anthracycline compound of the formula (I):

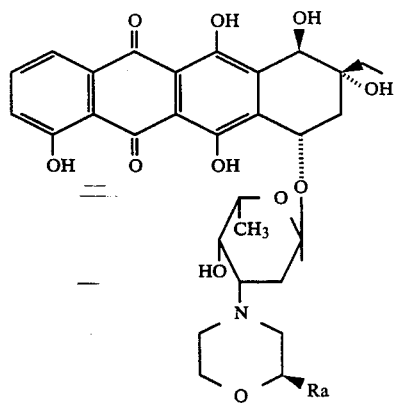

wherein Ra is —R$^1$,

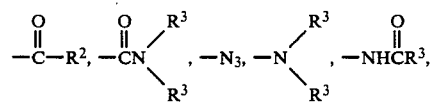

or —OR$^3$, R$^1$ being (1) alkyl, alkenyl, alkynyl, fluoroalkyl, aryl or aralkyl, or (2) alkyl, alkenyl, alkynyl, fluoroalkyl, aryl or aralkyl having substituents selected from the group consisting of carboxyl, azido, amino, hydroxy, alkoxy and a halogen atom; R$^2$ being R$^1$, a hydrogen atom or hydroxy; and R$^3$, which may be the same or different when one substituent has two R$^3$'s, being R$^1$ or a hydrogen atom; or the formula (II):

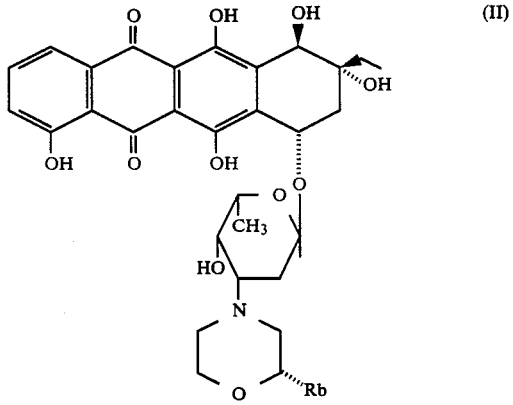

wherein Rb is —R$^1$,

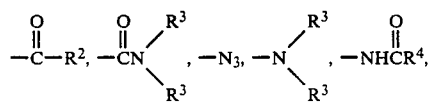

or —OR$^3$, R$^1$, R$^2$ and R$^3$ being as defined above; and R$^4$ being the same as R$^3$ except that methyl is not included; or an acid addition salt thereof.

2. An anthracycline compound according to claim 1, wherein Ra is —N$^3$,

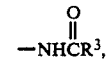

or —OR$^3$, R$^3$ being alkyl or fluoroalkyl.

3. An anthracycline compound according to claim 1, wherein Rb is —N$^3$,

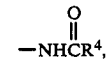

or —OR$^3$, R$^3$ being alkyl or fluoroalkyl and R$^4$ being fluoroalkyl.

4. A compound according to claim 1, which is 3'-Deamino-3'-[2''S)-2''-azido-4''-morpholino]-R20X2.

5. A compound according to claim 1, which is 3'-Deamino-3'-[(2''R)-2''trifluoroacetimido-4''-morpholino]-R20X2.

6. A compound according to claim 1, which is 3'-Deamino-3'-[2''S)-2''-acetamido-4''-morpholino]R20X2.

* * * * *